(12) United States Patent
Weigt

(10) Patent No.: US 9,797,833 B2
(45) Date of Patent: Oct. 24, 2017

(54) METHOD FOR DETERMINING THE REFRACTIVE POWER OF A TRANSPARENT OBJECT, AND CORRESPONDING DEVICE

(71) Applicant: ISRA SURFACE VISION GMBH, Herten (DE)

(72) Inventor: Paul Weigt, Bochum (DE)

(73) Assignee: ISRA SURFACE VISION GMBH, Herten (DE)

( * ) Notice: Subject to any disclaimer, the term of this patent is extended or adjusted under 35 U.S.C. 154(b) by 178 days.

(21) Appl. No.: 14/893,176

(22) PCT Filed: May 27, 2014

(86) PCT No.: PCT/EP2014/060933
§ 371 (c)(1),
(2) Date: Nov. 23, 2015

(87) PCT Pub. No.: WO2014/191401
PCT Pub. Date: Dec. 4, 2014

(65) Prior Publication Data
US 2016/0109363 A1 Apr. 21, 2016

(30) Foreign Application Priority Data
May 29, 2013 (DE) .......... 10 2013 105 570

(51) Int. Cl.
*G01N 21/00* (2006.01)
*G01N 21/41* (2006.01)
(Continued)

(52) U.S. Cl.
CPC ......... *G01N 21/41* (2013.01); *G01M 11/0228* (2013.01); *G01M 11/064* (2013.01);
(Continued)

(58) Field of Classification Search
CPC ............ G01M 11/064; G01M 11/0228; G01N 21/41; G01N 2021/9583; G01N 2021/9586
(Continued)

(56) References Cited

U.S. PATENT DOCUMENTS 3,880,525 A * 4/1975 Johnson ............. G01M 11/0235
356/127
5,128,550 A * 7/1992 Erbeck ................. G01N 21/958
250/559.01
(Continued)

FOREIGN PATENT DOCUMENTS

CN 1720444 1/2006
CN 102853784 1/2013
(Continued)

OTHER PUBLICATIONS

Commission Directive 2001/92/EC of Oct. 30, 2001, Official Journal of the European Comminities, Nov. 8, 2001.
(Continued)

*Primary Examiner* — Hoa Pham
(74) *Attorney, Agent, or Firm* — Michael J. Striker

(57) ABSTRACT

A method for determining a refractive power of a large-surface-area transparent object, such as a windshield, a visual aid, a cockpit glazing, a helmet visor, or the like, includes detecting a first imaging of a first line grating through the transparent object at at least one predetermined point of the object using a camera and determining a line spacing of the first imaging, the rotation of the lines relative to the first line grating or both through use of a computing unit on the basis of the first imaging at the at least one specified point and using the line spacing or rotation of lines to determine the refractive power at the at least one predetermined point of the transparent object.

15 Claims, 13 Drawing Sheets

(51) Int. Cl.
*G01M 11/02* (2006.01)
*G01M 11/06* (2006.01)
*G01N 21/958* (2006.01)

(52) U.S. Cl.
CPC ........... *G01N 2021/9586* (2013.01); *G01N 2201/062* (2013.01); *G01N 2201/12* (2013.01)

(58) Field of Classification Search
USPC .... 356/124–127, 237.1–237.5, 239.1, 239.4, 356/239.7, 239.8, 128–137
See application file for complete search history.

(56) References Cited

U.S. PATENT DOCUMENTS

| | | | | |
|---|---|---|---|---|
| 5,872,625 | A * | 2/1999 | Kajino | G01M 11/0235 356/124 |
| 6,208,412 | B1 * | 3/2001 | Ladewski | G01N 21/958 356/124 |
| 6,509,967 | B1 * | 1/2003 | Pingel | G01N 21/455 356/239.1 |
| 7,495,760 | B2 * | 2/2009 | Miyake | G01N 21/896 356/239.1 |
| 9,212,991 | B2 | 12/2015 | Saito et al. | |
| 2003/0049693 | A1 | 3/2003 | Goh et al. | |
| 2011/0187855 | A1 * | 8/2011 | Pichon | G01B 11/2513 348/136 |

FOREIGN PATENT DOCUMENTS

| | | |
|---|---|---|
| CN | 103080729 | 5/2013 |
| DE | 2310763 | 9/1974 |
| DE | 3600199 | 7/1986 |
| DE | 3937559 | 3/1991 |
| DE | 19643017 | 4/1998 |
| DE | 29724139 | 2/2000 |
| EP | 0416302 | 3/1991 |
| EP | 2101143 | 9/2009 |
| EP | 2 607 886 | 6/2013 |
| GB | 2152210 | 7/1985 |
| JP | 63-21539 | 1/1988 |
| JP | 63-210646 | 9/1988 |
| JP | 2006-264495 | 10/2006 |
| WO | WO 2013/059428 | 4/2013 |

OTHER PUBLICATIONS

ECE R 43, Agreement Concerning the Adoption of Uniform Technical Prescriptions for Wheeled Vehicles . . . , Feb. 11, 2004.

* cited by examiner

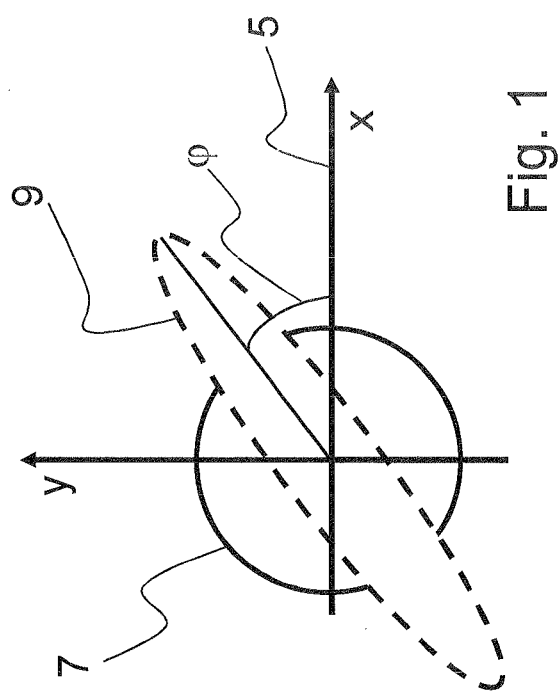
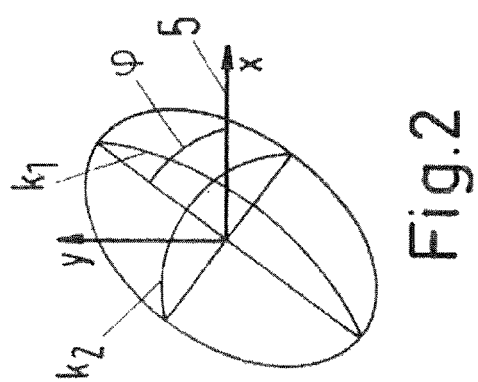
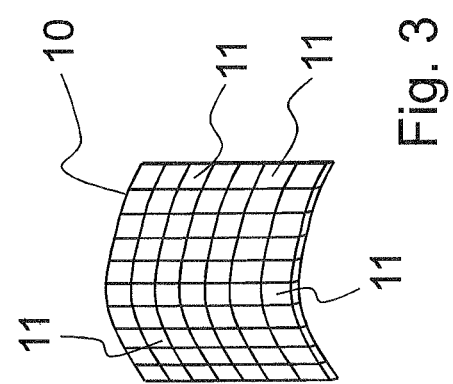

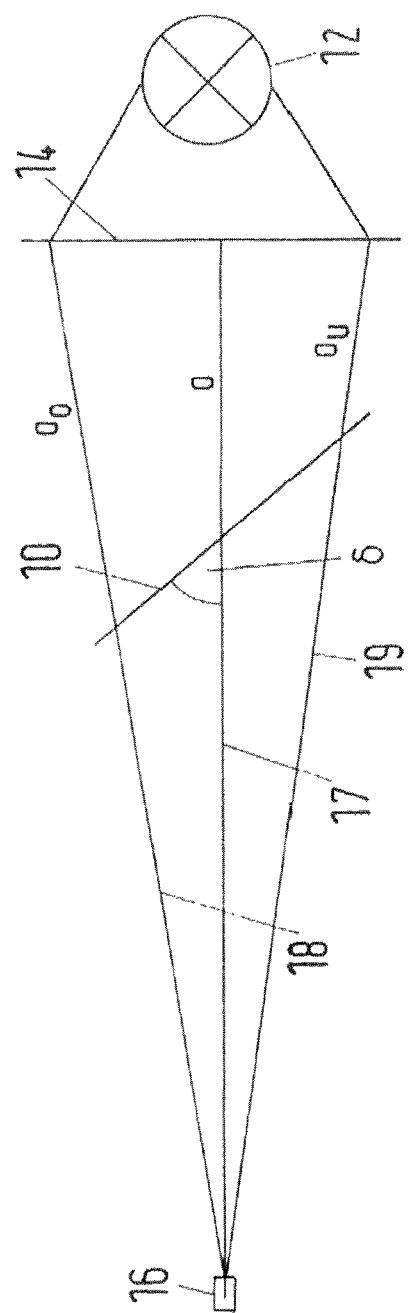

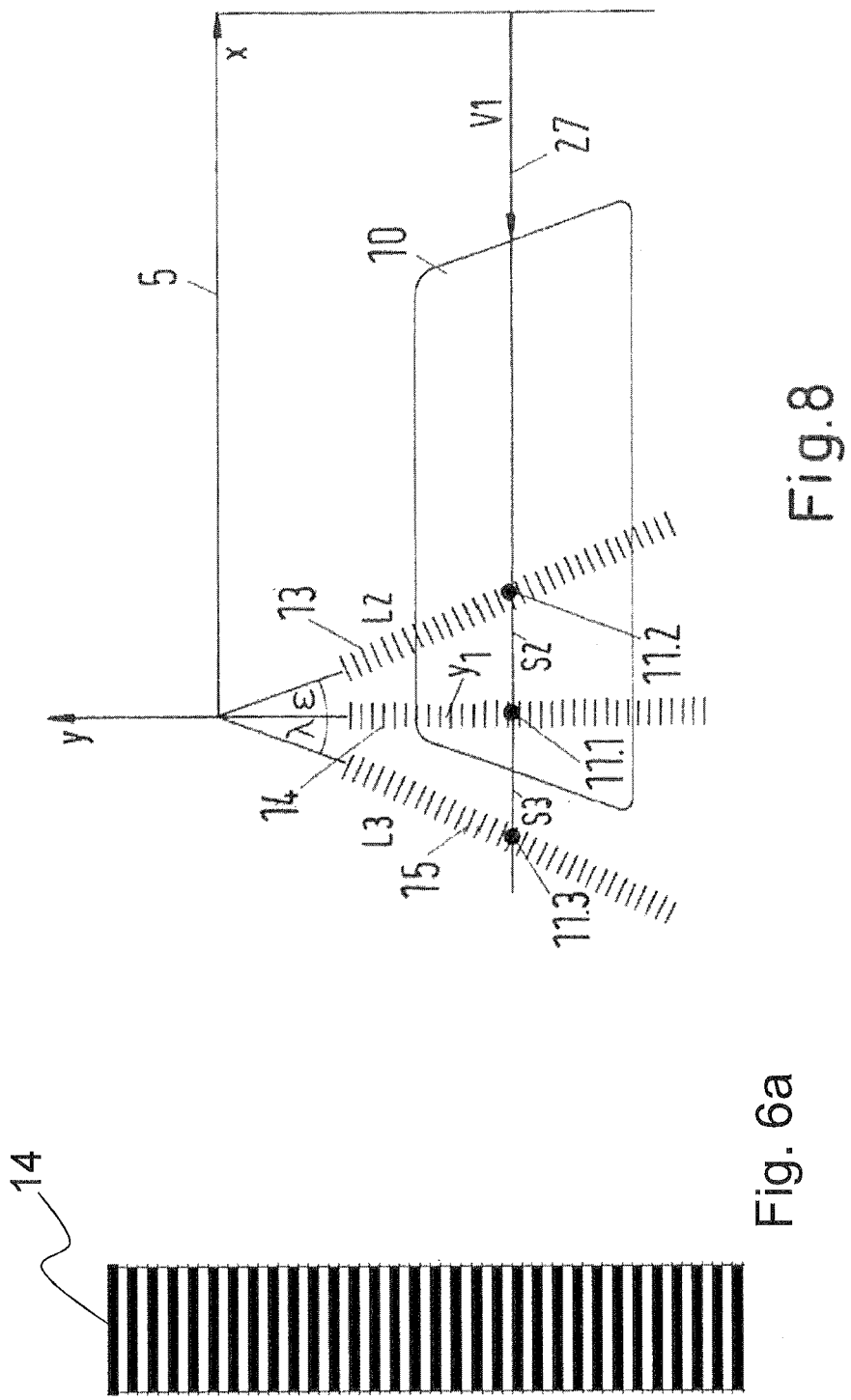

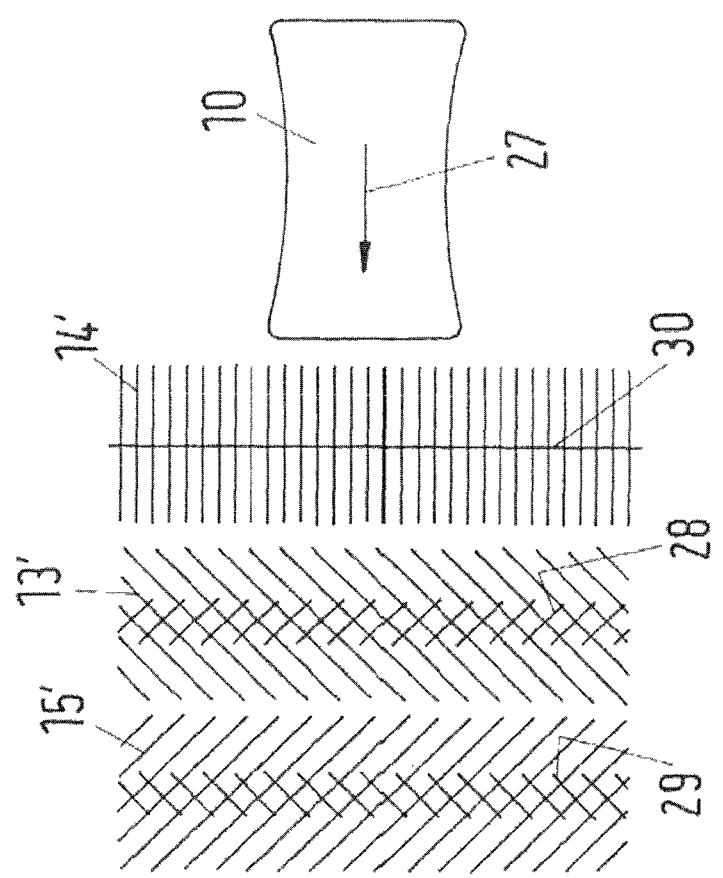

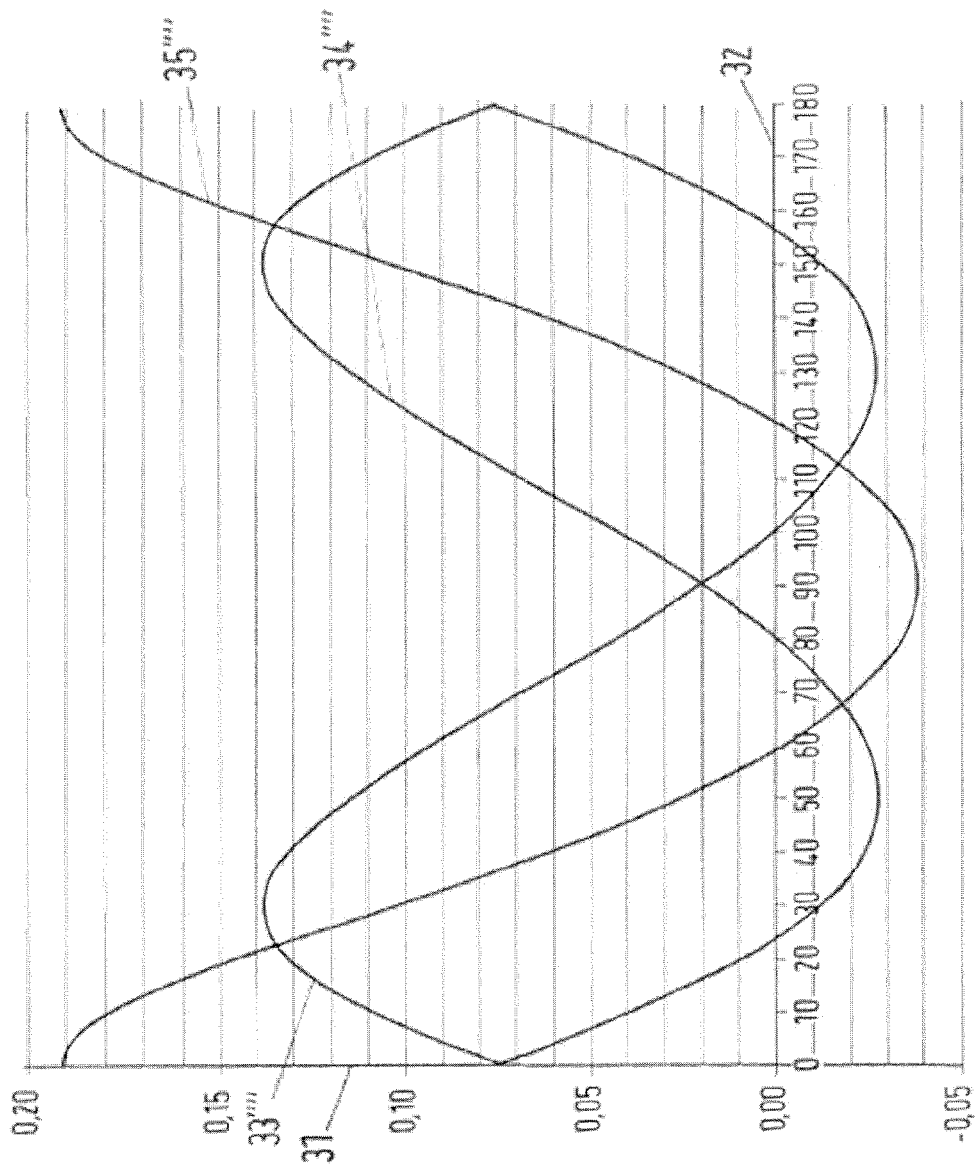

METHOD FOR DETERMINING THE REFRACTIVE POWER OF A TRANSPARENT OBJECT, AND CORRESPONDING DEVICE

CROSS-REFERENCE TO A RELATED APPLICATION

The invention described and claimed hereinbelow is a National Stage Application of PCT/EP2014/060933, filed May 27, 2014 (the PCT application), under 35 USC §371. The PCT application claims priority from German Patent Application DE 10 2013 105 570.2, filed on May 29, 2013. The German priority application and the PCT application are incorporated herein by reference and provide the basis for a claim of priority of invention.

BACKGROUND OF THE INVENTION

The present invention relates to a method for determining the refractive power of a transparent object, e.g., a windshield, a visual aid, a cockpit glazing, a helmet visor, or the like, and to a corresponding device.

The maximum refractive powers permitted in the windshield (WSS) are defined in statutory requirements such as ECE R43 or Directive 2001/92/EC and must be complied with by the manufacturers of the glass panes or the corresponding vehicles.

In order to measure the refractive power of such glass panes, a method is known in which a grating having a multiplicity of circular disks disposed at fixed distances of, e.g., 24 mm, and each having a diameter of, e.g., 8 mm, is projected through a windshield onto a screen. In this method, the magnitude of the deformation of the projected bright circular disks is a measure of the spatial distribution of refractive powers present in the glass pane. In the projection through a glass pane with a non-spherical lens (general case), every circular disk of the grating is distorted into an ellipse rotated through an angle φ. In other words, the circular disk is, e.g., compressed in one direction and is lengthened in the other direction. The deformation of the circular disk 7 into an ellipse 9 is shown in FIG. 1. When spherical lenses are used, the circular disks are enlarged or reduced in size.

Using the known circle grating method, it is therefore possible to determine the extreme values of the refractive powers directly in the points of the windshield selected for the projection of the circular disks by measuring the axes of the ellipse or the diameter of the circle. The position of the non-spherical lens is given by the angle φ, which can also be measured. The lens coordinate system is rotated through the angle φ relative to the measurement coordinate system.

The known method has the disadvantage, however, that the circular disks have a certain, predetermined distance from one another, as indicated above, i.e., in order to measure the entire windshield, a plurality of measurements must be carried out in which the grating is displaced relative to the windshield. In so doing, investigators attempt to manually fix the position of the circular disks in such a way that the circular disks detect the regions having the extreme values of the refractive powers. A template on the screen is subsequently used to determine whether the refractive power of the windshield deviates from the requirements or not at the corresponding points on the windshield. This is a highly complex procedure with a high susceptibility to error.

SUMMARY OF THE INVENTION

The problem addressed by the present invention is therefore that of providing a method, which makes it possible to easily determine the refractive power of a transparent object in an automated manner and with a low susceptibility to error. The problem is further that of creating a corresponding device for carrying out such a method.

The aforementioned problem is solved by a method and device provided in accordance with the invention.

According to the invention, a camera is used to capture a first imaging of a first line grating through the object at at least one predetermined point of the object (e.g., a windshield) and a central processing unit is subsequently used to determine, on the basis of the first imaging at the at least one predetermined point of the object, the line spacing of the first imaging and/or the rotation of the lines relative to the first line grating and, from this, to determine the refractive power at the at least one predetermined point of the object. In particular, the determination of the refractive power at the at least one predetermined point (in the corresponding volume element) of the object includes the determination of the refractive power in every azimuthal direction of this point, including the extreme values of the refractive power. Particularly preferably, according to the invention, the line spacing of the first imaging is determined transversely to the lines of the first line grating and, from this and with consideration for the rotation of the lines, the refractive power is determined at the at least one predetermined point of the object.

The preferable approach in this case is to simultaneously generate the first imaging of an, e.g., linear or striated line grating through a linear or striated region of the object, i.e., through a multiplicity of points of the object disposed on a line or in a strip. In order to determine the refractive power at every point of the entire object, the imagings of the line grating are determined in succession through all line or strip regions of the object arranged side-by-side.

Within the framework of the present invention, a point of the object means a volume element of the object having a certain refractive power. A volume element of an object, which is preferably disk-shaped and therefore has a relatively small expansion in one spatial direction (in the direction of the disk thickness), extends from the front side to the back side of the object and includes the entire thickness of the object. The entire object is composed of a multiplicity of volume elements, the behavior of which is approximated with the model of a lens, which shall be shown in the following.

The invention is based on the assumption that the curvature of a lens having any shape can be described by its principal curvatures $k_1$, $k_2$ at any point of the lens by the axes of an ellipse and the azimuthal position of the axes relative to a stationary, two-dimensional measurement coordinate system 5 (coordinates x,y) through the angle φ (see FIG. 2). The refractive power (refractive index) of such a lens having its surface curvatures $k_1$, $k_2$ can be approximated, e.g., by the following formula, which applies for biconvex lenses:

$$\frac{1}{f} = (n-1) \cdot \left[\frac{1}{r_1} + \frac{1}{r_2}\right] = (n-1) \cdot [k_1 + k_2], \quad (1)$$

in which f is the focal length of the lens, n is the refractive index, and the variables $r_1$, $r_2$ are the radii of curvature of the lens surfaces. The refractive power is 1/f and the curvature is 1/r. Assuming $k_1 = k_2 = k$ for a spherical lens and assuming a refractive power for glass of n=1.5, the following applies, for example:

$$\frac{1}{f} = \frac{1}{r} = k \quad (2)$$

For glass, the refractive power 1/f is therefore equal to the curvature k. Curvature is described by Euler's formula:

$$k = k_1 \cdot \cos^2\gamma + k_2 \cdot \sin^2\gamma \quad (3),$$

wherein the angle γ is an angle in the lens coordinate system, in which γ=0 is equivalent to k=$k_1$ and γ=90° is equivalent to k=$k_2$.

The invention makes use of the finding from Euler's formula (equation (3)) and FIG. 2 that the two principal curvatures $k_1$, $k_2$ and the orientation φ of the lens relative to the stationary coordinate system 5 must be known in order to fully characterize the curvature of any lens and, therefore, to characterize the refractive power at any point (in any volume element having the thickness h). In FIG. 3, a transparent body 10, e.g., a section of a windshield, is depicted as an example of subdividing the object into a multiplicity of volume elements, wherein this section is subdivided into 10×7 volume elements 11.

The method according to the invention is further based on the finding that lines of a line grating are azimuthally rotated and their line spacing is changed by a non-spherical lens. This means that, depending on the refractive power at the particular point, the image of the line grating has a different line spacing than the (original) line grating and, in addition, the lines of the image are rotated with respect to the (original) line grating. This is visible in the imaging of a line grating through the lens.

Images of a line grating through a cylindrical lens at selected angles are shown in FIG. 4 as an example of this effect. If the axis of the cylindrical lens points in the direction of the grating lines, the only change is a change in the line spacing. When the cylindrical axis is positioned perpendicularly to the grating lines, the grating lines are not changed. In all other cases, a rotation and a change in the line spacing takes place depending on the refractive power.

The above-described effect is utilized, according to the invention, in a grating method, by means of which the entire transparent object is detected element-by-element or point-by-point. The image of a first line grating is captured point-by-point using a camera. The central processing unit utilizes the image to determine the spacing of the lines and/or their rotation relative to the line grating. On the basis thereof, the refractive power at any point of the object can be determined by means of the central processing unit, as shall be explained in the following.

Within the scope of the description of the present invention, the line spacing refers to a line width of a black (dark) line or a black (dark) strip and/or a white (light) line or a white (light) strip arranged side-by-side in alternation, in the direction transversely to the lines. With respect to the present invention, when measuring the imaging of the line grating through the object, the line spacing is preferably determined perpendicularly to the lines of the particular line grating used for the measurement.

The imaging of an obliquely positioned line grating through a non-spherical lens ($k_1 \neq k_2$) is represented phenomenologically in FIG. 7. The lens is rotated azimuthally in front of the grating lines. It is apparent that the direction as well as the spacing of the grating lines change depending on the angle of rotation. The direction and spacing remain the same only in exceptional cases.

A lens having the main axes x' and y' (coordinate system 25) relative to a stationary coordinate system 5 is considered in detail in FIG. 7. The lens forms an image of a line grating 13, which is rotated through the angle σ relative to the stationary coordinate system 5. By means of the imaging of the lens, the line grating 13 is rotated such that the line grating 23 of the imaging forms the angle β with the stationary coordinate system 5. The line spacing g of the original line grating 13 becomes d in the coordinate system 25 of the image. Furthermore, the point (e, s) on the original line grating 13 is transformed with the factors ν and μ into the point (νe, μs) on the line grating 23 of the imaging. The point (0, s) is imaged onto (0, μs). The following relationships can be determined from FIG. 7:

$$\frac{g}{s} = \cos(\sigma - \varphi) \quad (4)$$

$$\frac{s}{e} = tg(\sigma - \varphi)$$

$$\frac{d}{\mu s} = \cos(\beta - \varphi)$$

$$\frac{d}{\nu e} = \sin(\beta - \varphi),$$

wherein the parameters have the following meaning:

σ=angle of the original line grating 13 (dashed lines) relative to the stationary coordinate system 5, φ=angle of rotation of the lens (of the lens coordinate system 25) with respect to the stationary coordinate system 5, β=angle of the imaged line grating 23 with respect to the stationary coordinate system 5.

The factors ν and μ result from the thin lens formulas.

$$\mu = \frac{1}{1 - a \cdot k_1} \quad (5)$$

$$\nu = \frac{1}{1 - a \cdot k_2}$$

Therein, a is the distance between the grating and the object to be measured (see FIG. 5). It is therefore also clear that this is not a moiré method, but rather the determination of strip widths and the rotation of strips by imaging using a lens.

The point (νe, μs) in the lens coordinate system will now be expressed as coordinates (x, y) in the stationary coordinate system. The coordinate systems are rotated with respect to one another through the angle φ, and so the following results:

$$\begin{pmatrix} x \\ y \end{pmatrix} = \begin{pmatrix} \cos\varphi & -\sin\varphi \\ \sin\varphi & \cos\varphi \end{pmatrix} \cdot \begin{pmatrix} \nu e \\ \mu s \end{pmatrix} = \begin{pmatrix} \nu e \cdot \cos\varphi - \mu s \cdot \sin\varphi \\ \nu e \cdot \sin\varphi + \mu s \cdot \cos\varphi \end{pmatrix} \quad (6)$$

$$tg\beta = \frac{y}{x} = \frac{\nu e \cdot \sin\varphi + \mu s \cdot \cos\varphi}{\nu e \cdot \cos\varphi - \mu s \cdot \sin\varphi} = \frac{\nu e \cdot tg\varphi + \mu s}{\nu e - \mu s \cdot tg\varphi} = \frac{\nu \cdot tg\varphi + \mu \cdot tg(\sigma - \varphi)}{\nu - \mu \cdot tg\varphi \cdot tg(\sigma - \varphi)} =$$

$$\frac{\nu \cdot \sin\varphi \cdot \cos(\sigma - \varphi) + \mu \cdot \sin(\sigma - \varphi) \cdot \cos\varphi}{\nu \cdot \cos\varphi \cdot \cos(\sigma - \varphi) - \mu \cdot \sin\varphi \cdot \sin(\sigma - \varphi)}$$

$$d = \mu \cdot g \cdot \frac{\cos(\beta - \varphi)}{\cos(\sigma - \varphi)} = \nu \cdot g \cdot \frac{\sin(\beta - \varphi)}{\sin(\sigma - \varphi)}$$

The line grating 23 imaged through a lens forms the angle β with the stationary coordinate system and d is the line width of the imaged grating. Critical points for d result at σ−φ=0° or 90°. Therefore, either the first or the second equation applies.

In the case of a horizontal grating, σ=0. Therefore:

$$tg\beta = \frac{(v-\mu) \cdot tg\varphi}{v + \mu \cdot tg^2\varphi} \quad (7)$$

$$d = \mu \cdot g \cdot \frac{\cos(\beta - \varphi)}{\cos\varphi} = -v \cdot g \cdot \frac{\sin(\beta - \varphi)}{\sin\varphi}$$

In the case of a spherical lens, v=μ. In this case, the following applies:

$$tg\beta = \frac{tg\varphi + tg(\sigma - \varphi)}{1 - tg\varphi \cdot tg(\sigma - \varphi)} = tg\sigma \quad (8)$$

$$d = \mu \cdot g$$

Since β=σ, the original grating is not rotated by a spherical lens. In the case of the horizontal grating, the line spacing is scanned perpendicularly to the grating lines of the original grating. Since the original grating is rotated via the imaging by a lens, it is not d, but rather $d_s$ that is preferably measured perpendicular to the lines of the first line grating (perpendicular scan) when determining the line spacing. The following applies:

$$d_s = \frac{d}{\cos\beta} \quad (9)$$

The measured value $M_h$ for a horizontal grating should be defined as the deviation of the perpendicularly measured line widths of the imaged line grating relative to the line width of the original line grating. Therefore, the following should apply:

$$M_h = d_s - g = \left[\frac{\mu \cdot \cos(\beta - \varphi)}{\cos\beta \cdot \cos\varphi} - 1\right] \cdot g = -\left[\frac{v \cdot \sin(\beta - \varphi)}{\cos\beta \cdot \sin\varphi} + 1\right] \cdot g \quad (10)$$

For a spherical lens as the object, as presented above, μ=v=m and, therefore, β=σ=0. Proceeding from equation (10), the following therefore results for the spherical lens:

$$M_h = d_s - g = [m-1] \cdot g \quad (11)$$

When measuring a spherical lens, it is therefore sufficient according to the invention to capture the imaging of a first line grating and evaluate this with respect to the change in the line spacing.

For arbitrary object shapes, i.e., any shape of a lens, the values for the principal curvatures $k_1$, $k_2$ and the angle φ are required and, therefore, three independent measurements are required, which are carried out successively or simultaneously. In order to obtain three independent measurements, the horizontal grating can be rotated through a certain, defined angle, wherein the line spacing is preferably determined perpendicular to the grating lines of the grating of the scanning device used for the measurement. In the simultaneous measurement, it must be possible to make a distinction between the images of the various line gratings in order to obtain independent measurements. This can be implemented, for example, by illuminating the line grating with light having a different wavelength and so the camera captures only the wavelength range of the particular imaging and is not sensitive to the wavelength of the other line gratings; therefore, the imagings of the other line gratings do not interfere.

In a preferred exemplary embodiment, a method is therefore carried out according to the invention in which the camera is used to additionally capture a second imaging of a second line grating and/or a third imaging of a third line grating through the object at the at least one predetermined point, wherein, if applicable, the lines of the second line grating extend at an angle not equal to 0° (or 180°) relative to the lines of the first line grating and/or, if applicable, the lines of the third line grating extend at an angle not equal to 0° (or 180°, preferably also not equal to 90°) relative to the lines of the first line grating and, if applicable, not equal to 0° (or 180° and preferably also not equal to 90°) relative to the lines of the second line grating and subsequently the line spacing of the second imaging and/or of the third imaging is determined by means of the central processing unit on the basis of the second imaging and/or the third imaging, respectively, and/or the rotation of the lines relative to the respective line grating is determined and these data are additionally used to determine the refractive power at the at least one predetermined point of the object. The line spacing of the second imaging and/or of the third imaging is preferably determined relative to the respective line grating and, on the basis thereof, the refractive power at the at least one predetermined point of the object is determined with consideration for the rotation of the lines in the imaging with respect to the original line grating.

The determination of the line spacing is preferably carried out in the second imaging perpendicularly (transversely) to the lines of the second line grating and, in the third imaging, perpendicularly (transversely) to the lines of the third line grating.

The corresponding measured values $M_r$ and $M_l$ (each of which is a deviation of the perpendicularly measured line widths of the corresponding imaged line grating relative to the line width of the respective original line grating) for the imaging of the second and the third line grating result analogously to equation (10), wherein the second line grating is rotated, for example, through the angle $\epsilon_1$ relative to the first line grating and the third line grating is rotated through the angle $\epsilon_2$ relative to the first line grating. As an alternative, the first line grating and/or the second line grating and/or the third line grating can extend parallel to one another (when the line gratings are rotated relative to one another) or can be disposed in a common plane. The advantage of this measurement arrangement is that three measurements are carried out for each point of the object, which measurements differ only with regard to the advance of the object, which corresponds to the spacing of the line grating. When the line gratings are rotated, the angle of rotation of the gratings relative to one another must additionally be taken into account.

In order to determine the measured values $M_r$, $M_l$ and $M_h$, the object is preferably moved past the first line grating and, if applicable, the second line grating and, if applicable, the third line grating, one after the other, and with the respectively associated camera. As an alternative, the line gratings can also be moved.

The three measured values $M_h$, $M_l$, $M_r$ can be used to uniquely calculate the three parameters $k_1$, $k_2$ and the angle φ of rotation of the line by means of an iteration method (e.g., Excel Solver). The unambiguousness can be preferably achieved by additionally applying the conditions "when $M_l<M_r$ it follows that $\phi<90°$ and when $M_l>M_r$ it follows that $\phi>90°$" (12)

When the principal curvatures $k_1$, $k_2$ and their azimuthal position $\phi$ are then available in the stationary coordinate system, the refractive power of a lens can be calculated at any angle of intersection using Euler's formula (equation (3)).

The light intensity required for the imaging of the line grating can be obtained by arranging a light source behind the first line grating and/or, if applicable, behind the second line grating and/or, if applicable, behind the third line grating, which light source emits light, preferably white light, through the respective line grating and onto the camera.

As an alternative, the device according to the invention can comprise a light wall having a matrix of light source elements, which are preferably designed as LEDs or OLEDs. With the aid of this light wall, the first line grating and/or the second line grating and/or the third line grating can be successively generated, e.g., by switching, and so no other light sources are required. As an alternative, the line gratings can also be simultaneously generated by LEDs or OLEDs of a different color. For this purpose, the light source elements are activated in such a way that a first part of the light source elements form the white or light lines and a second part of the light source elements forms the black or dark lines positioned between two white lines in each case. The line width is therefore limited to the width of one light source element.

For example, for reasons related to the applicable normative requirements, it may be necessary to arrange the transparent object not only perpendicular to the optical axis of the camera, but rather to analyze it at the inclination, for example, at which it is also installed in a product. For example, it may be required to determine the refractive power of a windshield at an inclination angle $\xi$ relative to the horizontal (=often the optical axis), at which said windshield is installed in the vehicle. In this case it is necessary to consider the inclination (tilt) of the object relative to the optical axis of the camera, specifically with regard to two aspects. First, the refractive powers increase with the inclination of the object. For this purpose, a suitable amplification factor can be taken into account in the calculation, which amplification factor can be determined in advance for a certain material for a certain angular range of the inclination of the object. Secondly, the distance of the object from the respective line grating changes along the object. The distance a of the respective point of the object from the respective line grating therefore must be taken into account (cf. equation (5)).

When the object is slanted at an angle $\xi$, for example about the x-axis (see FIG. 10), the components $e_1$ and $e_2$ of the refractive power intensify at a certain point of the object relative to an angle $\lambda_1$ and $\lambda_2$, wherein these angles are generally smaller than $\xi$ and $\lambda_1$ and assumes the angle $\xi$ for $\phi=90°$.

FIG. 10 shows the plane E1 (in the x-y-z coordinate system), which corresponds to the x-y plane in FIG. 7, i.e., a vertically positioned object. The plane $E_1$ is slanted through the angle $\xi$ about the x-axis and, in this manner, is slanted relative to the plane $E_2$ having the x-y"-z" coordinate system. The vectors $e_1$ and $e_2$ are in the plane $E_1$. The vectors $e''_1$ and $e''_2$ are in the plane $E_2$ and arose from the rotation of the vectors $e_1$ and $e_2$ about the x-axis. The angle $\lambda 1$ between the vectors $e_1$ and $e''_1$ and the angle $\lambda_2$ between the vectors $e_2$ and $e''_2$ are dependent on the angle of rotation $\phi$ and the angle of inclination $\xi$.

The corresponding amplification factors are calculated as follows:

$$V(\lambda_1) = \frac{\sqrt{n^2 - \sin^2\lambda_1} - \cos\lambda_1}{(n-1)\cdot\cos\lambda_1} \quad (13)$$

and $$V(\lambda_2) = \frac{\sqrt{n^2 - \sin^2\lambda_2} - \cos\lambda_2}{(n-1)\cdot\cos\lambda_2},$$

wherein $$\cos\lambda_1 = \cos^2\phi + \sin^2\phi\cdot\cos\xi$$

and $$\cos\lambda_2 = \cos^2\phi + \sin^2\phi\cdot\cos\xi \quad (13a).$$

On the basis thereof, the factors $\mu$ und $\nu$, which are relevant for the imaging of the grating, can be calculated as follows:

$$\mu = \frac{1}{1 - a\cdot V(\lambda_2)\cdot k_1} \quad (14)$$

$$\nu = \frac{1}{1 - a\cdot V(\lambda_1)\cdot k_2}$$

The rotation of the grating lines tg $\beta$ and the measured value $M_h$ can then be determined in an analogous manner on the basis of the equations (7) and (10).

The aforementioned problem is further solved by a device having the features of claim 7.

The device comprises, in particular, a camera, a first, preferably striated or linear line grating, wherein the camera captures the first imaging of the first line grating through the object point-by-point, preferably in a linear or striated region, and comprises a central processing unit, wherein the central processing unit subsequently determines, on the basis of the first imaging, the line spacing of the first imaging and/or the rotation of the lines relative to the first line grating and, on the basis thereof, determines the refractive power at the particular point (in the particular volume element) of the object. The line spacing of the first imaging in a direction transverse to the lines of the first line grating is preferably detected by reference to the first imaging and, on the basis thereof, the refractive power at the particular point (in the particular volume element) of the object is determined with consideration for the rotation of the lines.

The advantages of such a device were explained above with respect to the method according to the invention.

As described above, it is advantageous when, in addition, a second line grating is provided for generating a second imaging through the object and/or a third line grating is provided for generating a third imaging of a third line grating through the object at the particular point, wherein, if applicable, the lines of the second line grating extend at an angle not equal to 0° (or 180°, preferably also not equal to 90°) with respect to the lines of the first line grating and/or, if applicable, the lines of the third line grating extend at an angle not equal to 0° (or 180°, preferably also not equal to 90°) with respect to the lines of the first line grating and, if applicable, not equal to 0° (or 180°, and preferably also not equal to 90°) with respect to the lines of the second line grating and subsequently, by means of the central processing unit, the line spacing of the second imaging and/or of the third imaging is determined on the basis of the second imaging and/or the third imaging, respectively, and/or the rotation of the lines relative to the respective line grating is determined and these data are additionally used to determine the refractive power at the particular point of the object. The line spacing of the second imaging and/or of the third imaging is preferably determined relative to the respective line grating and, on the basis thereof, the refractive power at the at least one predetermined point of the object is determined with consideration for the rotation of the lines.

It is further preferred when the camera is designed as a matrix camera or a line scan camera and when the device according to the invention preferably comprises a separate camera for the imaging of the first line grating, of the second line grating, if applicable, and of the third line grating, if applicable, wherein the camera is preferably arranged and the central processing unit is operated in such a way that the line width is determined perpendicular to the respective line grating.

BRIEF DESCRIPTION OF THE DRAWINGS

The invention is explained in the following in greater detail on the basis of exemplary embodiments and with reference to the figures. All the features that are described and/or graphically depicted form the subject matter of the invention, either alone or in any combination, independently of their wording in the claims or their back-references.

Schematically in the drawings:

FIG. 1 shows the distortion of a circular disk by the refractive power of a transparent object into an ellipse according to a method according to the prior art, FIG. 2 shows the behavior of the lens model at any point of the object having two principal curvatures $k_1$ and $k_2$ in a stationary coordinate system, FIG. 3 shows a perspective view from the side of a section of a transparent object, e.g., a windshield, subdivided into points (volume elements), FIG. 5 shows a view from the side of an exemplary embodiment of a device according to the invention, FIG. 6a shows a view from the front of a striated line grating, FIG. 8 shows a view from the direction of the camera of a device according to the invention for the first exemplary embodiment, represented in FIG. 6, of a method according to the invention, FIG. 9 shows a view from the direction of the camera of a second exemplary embodiment of a method according to the invention, FIG. 16 shows the curves according to FIG. 11 with $k_1=0.08$ m$^{-1}$, $k_2=-0.02$, a grating rotation of $\epsilon_1=45°$, $\epsilon_2=-45°$ and an inclination $\xi=50°$ and a=1 m.

DETAILED DESCRIPTION OF THE INVENTION

The exemplary embodiment of a device according to the invention shown in FIG. 5 shows a transparent object, e.g., in the form of a windshield 10 for a motor vehicle, which is disposed between a horizontal, striated line grating 14 and a camera 16. The horizontal line grating 14 is illuminated on the side opposite the windshield 10 by a light source 12, e.g., in the form of a fluorescent lamp, which has a constant intensity along its length. The pattern of the line grating 14 is refracted at the windshield and is imaged onto the camera 16. A striated line grating used for such a measurement is shown in greater detail in FIG. 6a.

Figure 4:
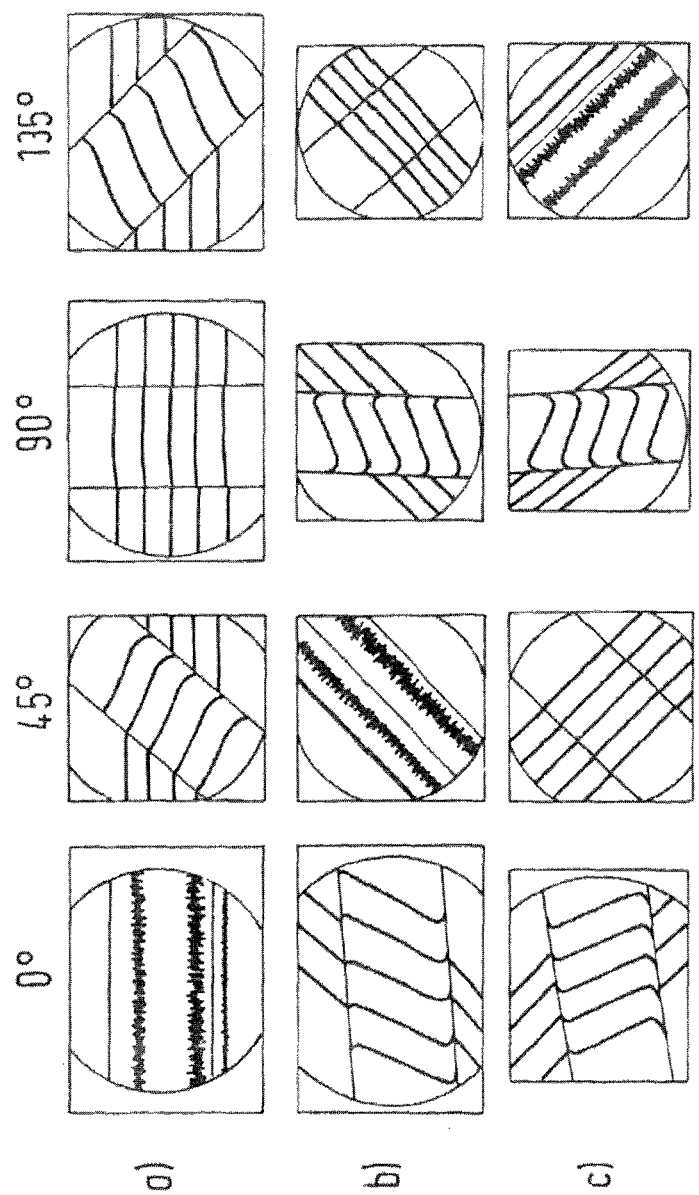
FIG. 4 shows photographs of the imaging of a line grating through a cylindrical lens for a horizontal grating (a)), a grating rotated obliquely to the right (b)) and a grating rotated obliquely to the left (c)) for arrangements of the cylindrical lens at various angles relative to the horizontal (see header)
Figure 7:
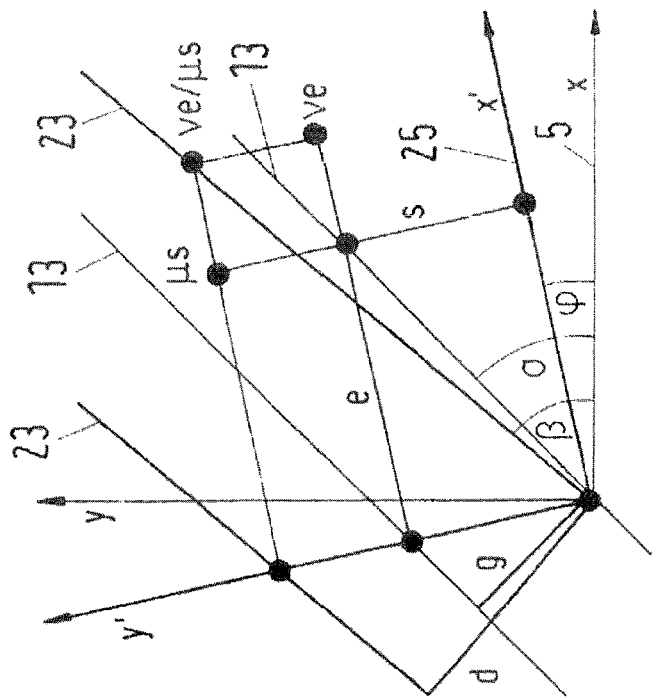
FIG. 7 shows a detailed view of the imaging of a line grating through a lens according to the method according to the invention.
Figure 6:
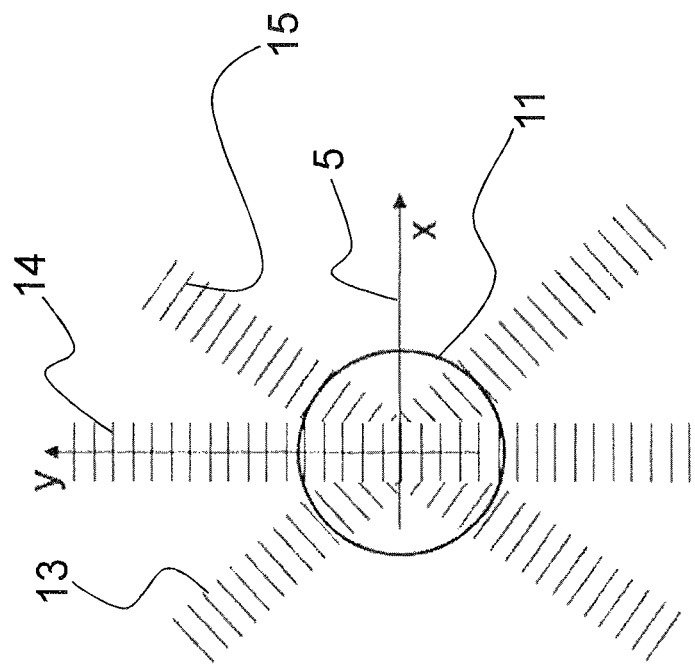
FIG. 6 shows a schematic diagram, in a view from the direction of the camera, of the procedure for a first exemplary embodiment of a method according to the invention.
Figure 10:
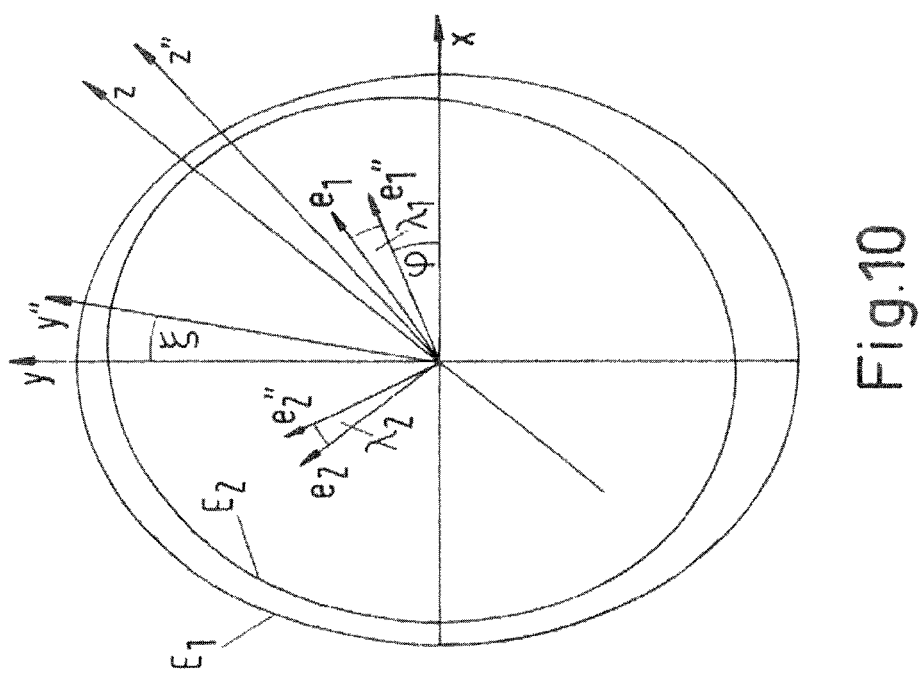
FIG. 10 shows the change of the position vector in two planes at a point in the lens coordinate system when the object is tilted.

In a first exemplary embodiment of the method according to the invention, three striated line gratings 13, 14, and 15, which are rotated relative to one another and which are represented in FIGS. 6 and 8, are used to determine the local refractive index over the entire windshield 10, which is composed of a multiplicity of points (volume elements) 11, as represented in a cutout in FIG. 3. The right line grating 13 is rotated through the angle $\epsilon_1=-30°$ relative to the horizontal line grating and the left line grating 15 is rotated through the angle $\epsilon_2=30°$. The lines of the line gratings 13, 15 are also rotated relative to the horizontal about the same respective angles.

A striated line grating 14 used for such a measurement is also represented in FIG. 6a. The striated line gratings 13, 15, which are rotated only with respect to the line grating 14, are also rotated in an analogous manner.

As was extensively described above in the general part of the description, three independent measurements must be performed successively or simultaneously using three line gratings rotated relative to one another (cf. FIGS. 6 and 8), which are arranged in a plane, for each point 11 of the windshield 10 in order to determine the curvatures k1, k2 and the angle $\phi$ or the refractive index. For this purpose, the windshield 10 is moved past the line gratings 13, 14, 15, which are arranged side-by-side or above one another, at a certain, predetermined speed. In the case shown in FIG. 8, the windshield has already been moved by the distance V1 for analysis purposes. The motion direction of the windshield 10 is indicated in FIG. 8 by the arrow 27. For the horizontal line grating 14, the point 11.1 is located at the grating position $y_1$ and at the advance of the glass pane V1. The following equations result from the geometric relationships in FIG. 8:

$$L2 = \frac{y_1}{\cos\varepsilon} \tag{14}$$

$$S2 = y_1 \cdot tg\varepsilon$$

$$L3 = \frac{y_1}{\cos\lambda}$$

$$S3 = y_1 \cdot tg\lambda$$

The measured value associated with the point 11.2 on the right line grating 13 is obtained at the position L2 and the advance Vr=V1−S2. On the left line grating, the measurement is carried out at the position L3 and the advance Vl=V1+S3.

As an alternative, the refractive index can also be measured in the vicinity of the horizontal grating 14' by means of an oblique line grating 13', 15', as shown in FIG. 9. In this exemplary embodiment, the line gratings 13', 15' extend parallel to the line grating 14', although the lines of the particular gratings are rotated relative to one another. In this case, the line spacing after the imaging through the windshield 10 is determined (scanned) by means of a matrix camera at every point perpendicular to the grating lines of the line gratings 13', 15'. The particular scanning direction is indicated in the center of the line grating 13', 14', 15' using one or more lines 28, 29, 30, respectively. Such an arrangement has the advantage that three measurements can be carried out for every point 11 of the windshield 10, which measurements differ only with regard to the advance of the glass pane, which corresponds to the separation of the line gratings 13', 14', 15'.

As another alternative, switchable lighting means can be used to generate the line gratings 13', 14', 15' at a point and to capture the three imagings at this point. In this exemplary embodiment, the switchable lighting means can also be used to generate the two oblique line gratings 13', 15' in temporal succession, e.g., at the point of the horizontal line grating 14'. Three imagings would then have to be captured by a matrix camera, also in temporal succession. The imagings can be evaluated in the desired scanning directions.

In FIG. 8, the following should apply: $\varepsilon_1=\varepsilon_2=\varepsilon$. If the lens is rotated in front of the grating, the left line grating 15 would not start the measurement at $\phi$ as it would with the horizontal line grating, but rather at $\phi+\varepsilon$. With regard to the right line grating 13, the measurement begins at $\phi-\varepsilon$. (In FIG. 9, the right line grating 15' and the left line grating 13' are interchanged as compared to FIG. 8.)

Based on the relationships in FIG. 9, the refractive power for each point is calculated from the measured values $M_h$, $M_l$ and $M_r$ using the following equations:

$$M_h = \left[\frac{\mu \cdot \cos(\beta-\varphi)}{\cos\beta \cdot \cos\varphi} - 1\right] \cdot g = -\left[\frac{v \cdot \sin(\beta-\varphi)}{\cos\beta \cdot \sin\varphi} + 1\right] \cdot g \tag{15}$$

$$M_l = \left[\frac{\mu \cdot \cos(\beta-\varphi-\lambda)}{\cos\beta \cdot \cos(\varphi+\lambda)} - 1\right] \cdot g = -\left[\frac{v \cdot \sin(\beta-\varphi-\lambda)}{\cos\beta \cdot \sin\varphi(\varphi+\lambda)} + 1\right] \cdot g$$

$$M_r = \left[\frac{\mu \cdot \cos(\beta-\varphi+\lambda)}{\cos\beta \cdot \cos(\varphi-\lambda)} - 1\right] \cdot g = -\left[\frac{v \cdot \sin(\beta-\varphi+\lambda)}{\cos\beta \cdot \sin\varphi(\varphi-\lambda)} + 1\right] \cdot g$$

In the following, the measured values are graphically depicted using the following parameters:

$\varepsilon_1=\varepsilon_2=45°$,
$k_1=0.080$,
$k_2=-0.020$,
$a=1$ m,
$g=1$ mm.

Figure 11:
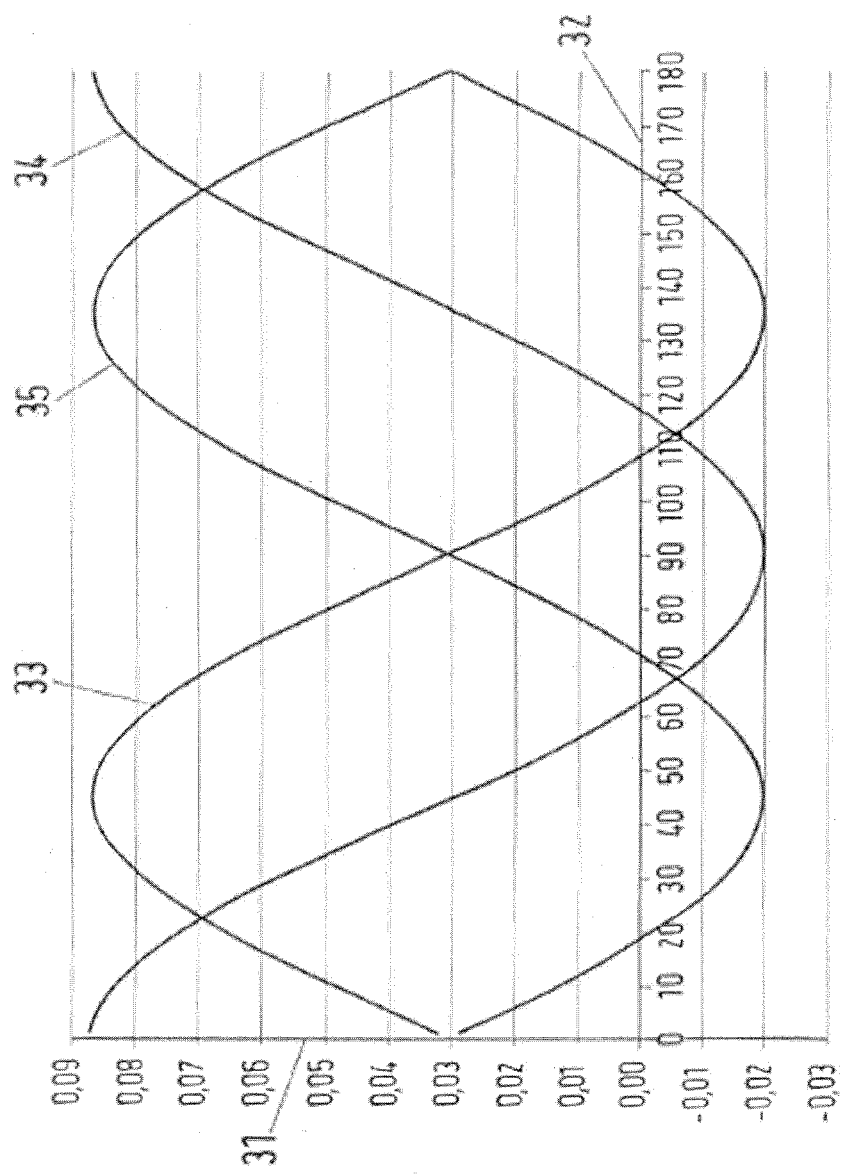
FIG. 11 shows curves for calculated refraction indices in [m$^{-1}$] for a horizontal grating, a right grating, and a left grating, wherein the scanning direction extends perpendicular to the grating lines in each case (for $M_l<M_r$ it follows that $\phi<90°$, for $M_l>M_r$ it follows that $\phi>90°$), plotted against the azimuthal angle which a lens can assume at a point of an object.

This results in the curves in FIG. 11, in which the curve for the measured value $M_r$ is labeled with reference number 33, the curve for the measured value $M_h$ is labeled with the reference number 34, and the curve for the measured value $M_l$ is labeled with the reference number 35, wherein $M_l<M_r$ applies when $\phi<90°$. $M_l>M_r$ applies when $\phi>90°$. The x-axis 32 in the diagram in FIG. 11 indicates the angle of rotation of the lens formed at the particular point, in [°], and the y-axis 31 indicates the measured value $M_h$, $M_r$ and $M_l$ in $[m^{-1}]$.

Figure 12:
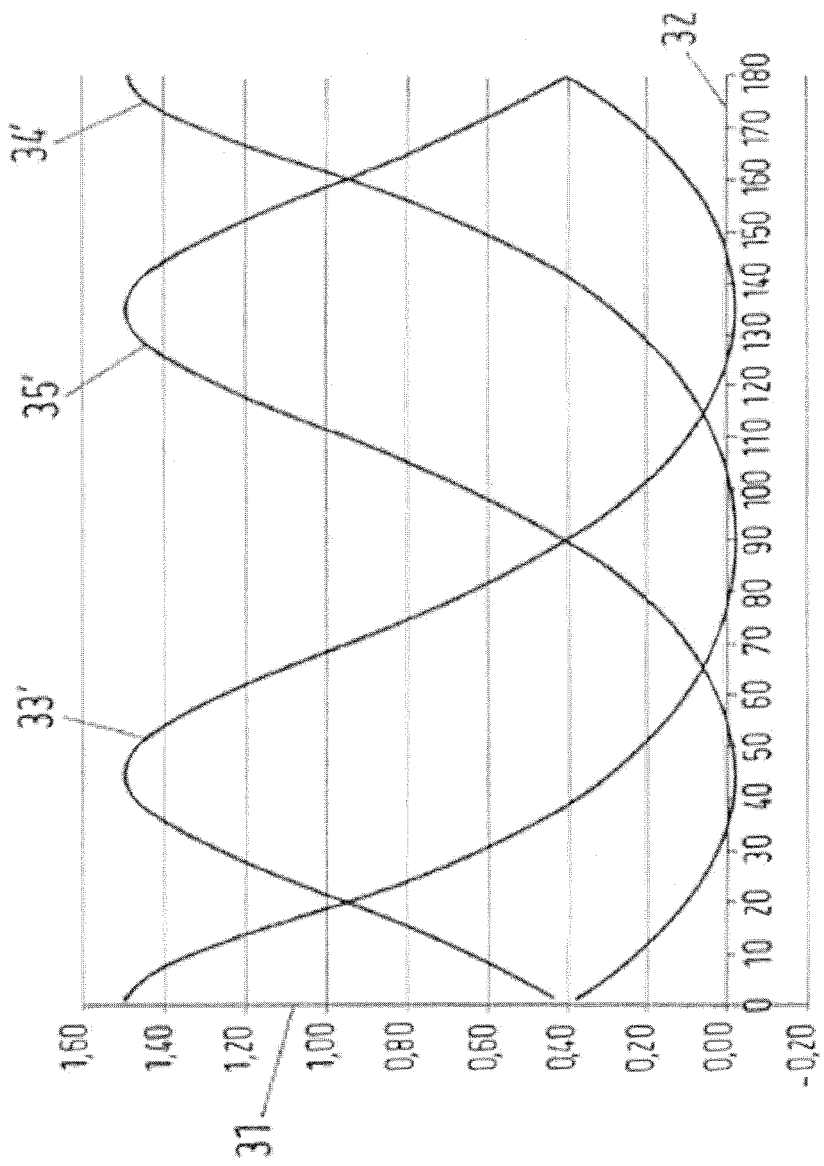
FIG. 12 shows the representation according to FIG. 10, but with $k_1=0.6$ m$^{-1}$.

The curves become distorted when it is assumed that $k_1=0.6$ m$^{-1}$, as shown in FIG. 12. If the focal length of the lens is equal to the distance a between line gratings 13', 14', 15' and the windshield 10, a measurement is no longer meaningful. The distance a should be less than the focal length of the lens. It therefore makes sense to shorten the distance a in a timely manner as the refractive powers increase.

Figure 13:
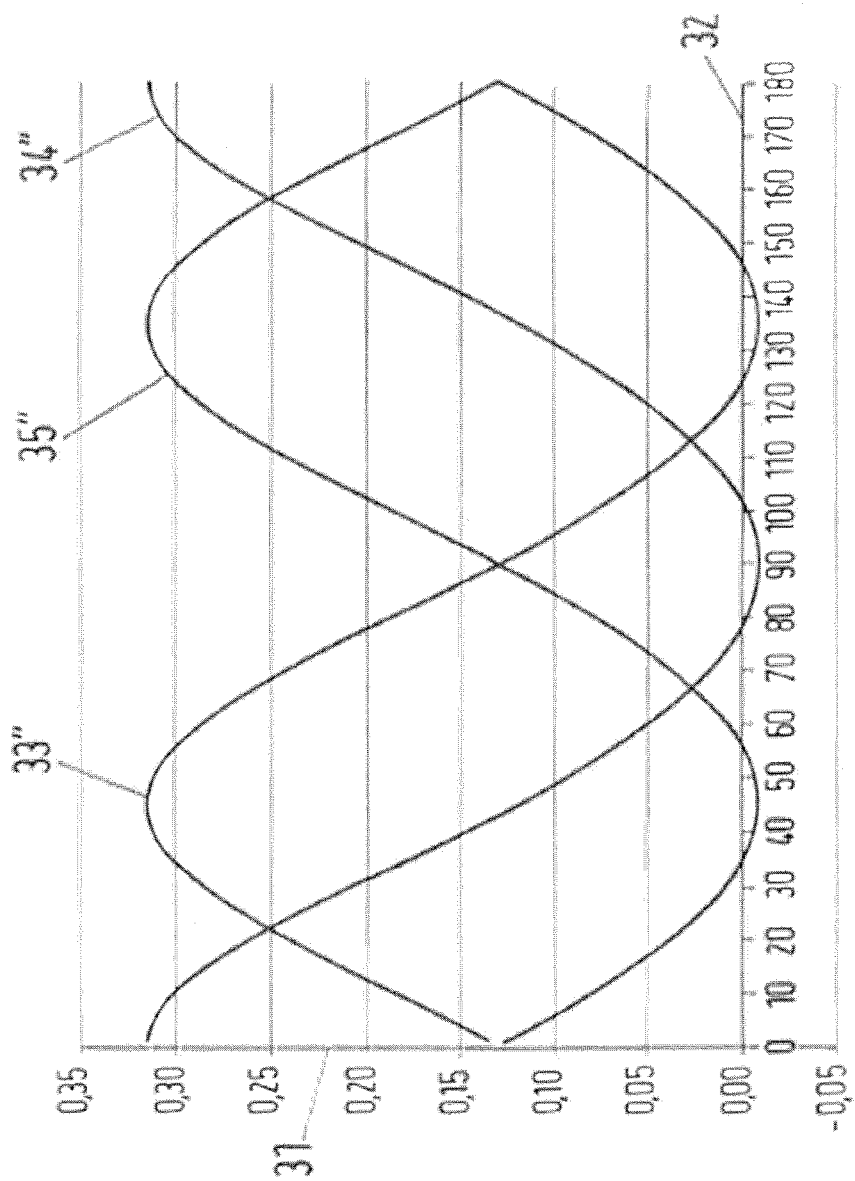
FIG. 13 shows the curves according to FIG. 11 in a representation according to FIG. 10, but with a distance a between the line grating and the transparent object of 0.4 m.

These distortions are avoided when the distance a between the line gratings 13', 14', 15' and the windshield 10 is shortened to 0.4 m. This is shown in the curves in FIG. 13.

Figure 14:
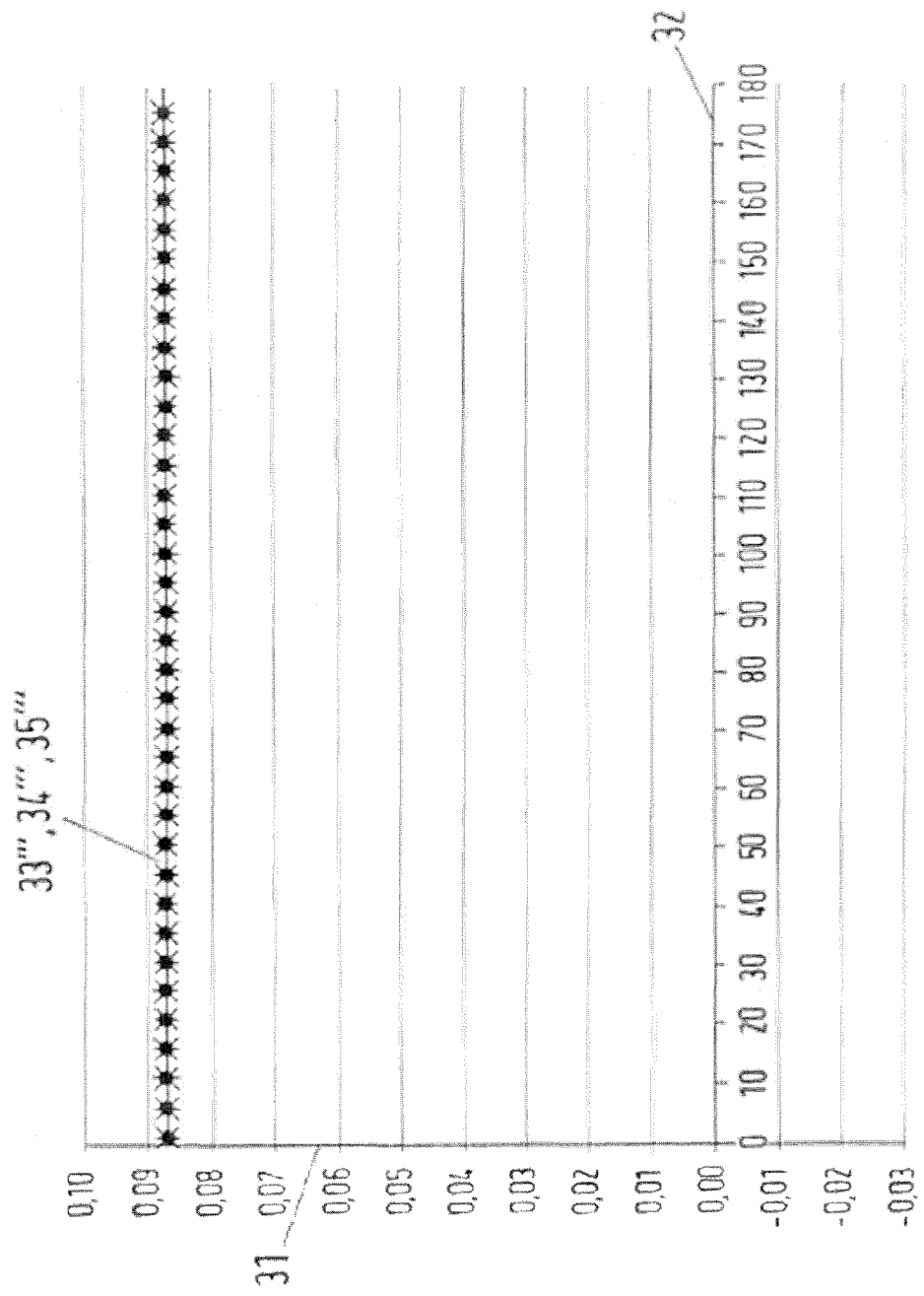
FIG. 14 shows the representation according to FIG. 10 for a spherical lens, wherein $k_1=k_2=0.08$ m$^{-1}$.
Figure 15:
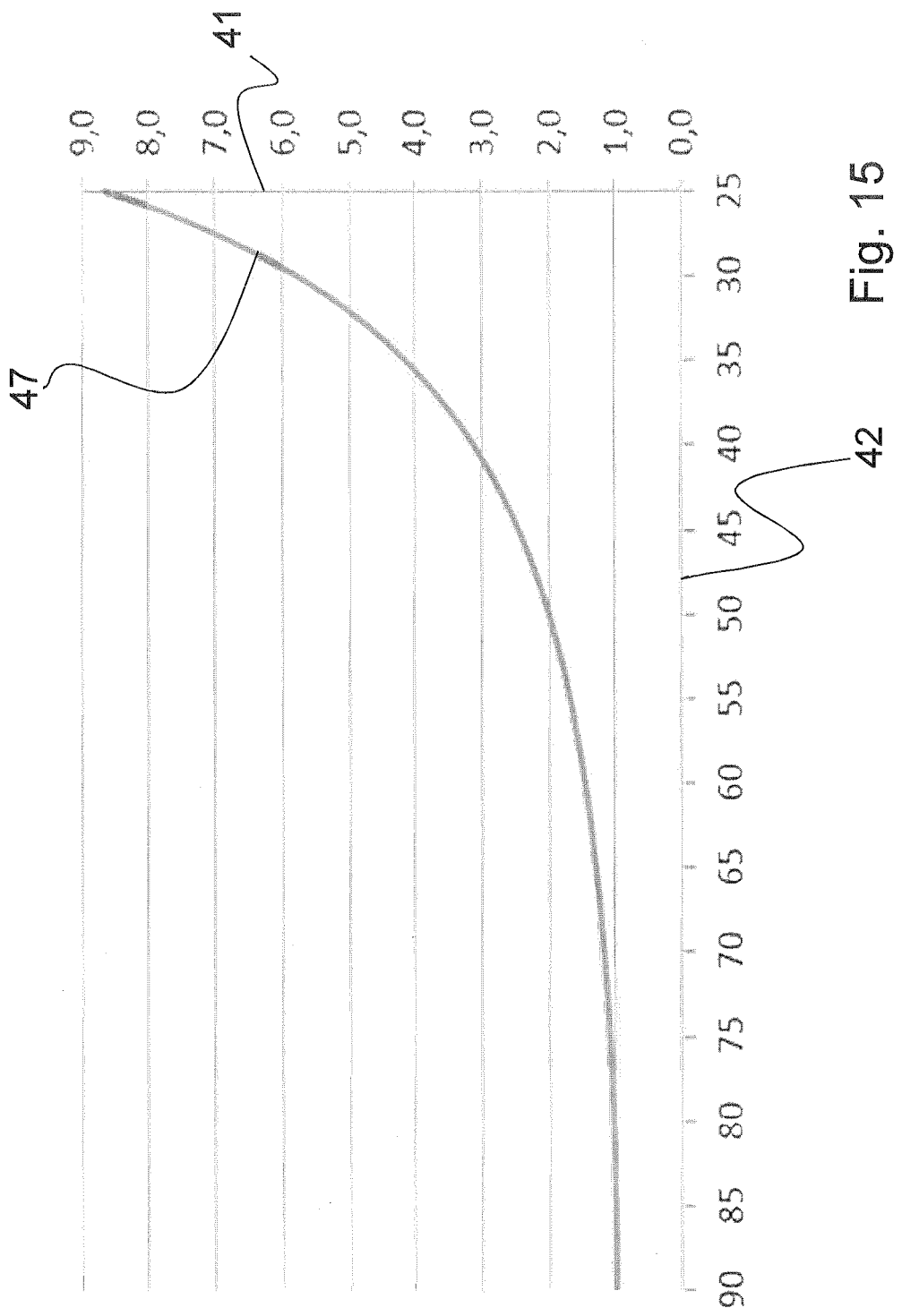
FIG. 15 shows the amplification factor for determining the refractive index plotted against the inclination angle $\xi$ of the transparent object made from glass having a refractive index n=1.5.

For a spherical lens, all the measured values are the same when the line spacings of the line gratings 13', 14', 15' are the same. This is illustrated in FIG. 14. The set of parameters used to calculate the curves in FIG. 11 was changed by $k_1=k_2=0.08$ m$^{-1}$.

The methods described so far relate to the measurement of a vertically positioned glass pane in front of a vertical grating. In many cases, it is necessary to measure a slanted (tilted) windshield 10, e.g., in the installed position. The measurement arrangement used for this purpose is represented in FIG. 5. FIG. 11 further shows the change in refractive power of a lens at a point when the object is slanted by the angle $\xi$ about the x-axis of the three-dimensional coordinate system having the axes x, y and z.

For glass having the refractive index n=1.5, the equation (12) indicated above can be used to calculate the amplification factor V, which is represented in FIG. 14 by the curve 47 over the axis 42, wherein the angle of inclination $\xi$ of the windshield 10 is plotted on the axis 42. This is taken into account by the non-illustrated central processing unit in the determination of the refractive power at the points 11 of the windshield 12. It is also apparent from FIG. 5 that, due to the slant of the windshield 10 relative to the optical axis 17, the distance $a_o$ of the windshield 10 to the line grating 14 in the region of an upper edge beam 18 changes to the distance a in the region of the optical axis 17 and ultimately to the distance $a_u$ in the region of a lower edge beam 19 of the imaging. This distance change of the slanted windshield 10 along its entire height has already been taken into account in the formulas.

A lens rotated from the plane $E_1$ into the plane $E_2$ can assume all possible azimuthal positions as is the case for the lens in the plane $E_1$. The lens is rotated through the angle $\phi$ in order to visualize the possible measured values. Greater extreme values are obtained with the vertical scan ($M_h$) than with the scans performed at a rotated angle ($M_r$, $M_l$). A principal curvature with maximum rotation is measured only with the vertical scan. If the glass pane is not slanted, the extreme values for all measurements are the same.

FIG. 16 corresponds to the above-described FIG. 11, with the following parameters:

$k_1=0.08$, $k_2=-0.02$,

Grating rotation $\epsilon_1=45°$ (curve 33"") and $\epsilon_2=-45°$ (curve 34""), Glass pane inclination $\xi=50°$ and Distance: grating-center of glass pane a=1 m, wherein the object (glass pane) was slanted by the angle $\xi$ with respect to the optical axis. The measurement is carried out in the center of the glass pane. The curve labeled with reference number 35"" corresponds to measurements carried out using the vertical grating. In this case, the extreme values of the curves 33"" and 34"" are the same, because the gratings were rotated through the same angle symmetrically with respect to the vertical grating. These extreme values are lower, however, than the extreme values for the measurement carried out using the vertical grating (see curve 35""). The reason for the different extreme values for a vertical scan and for the scan carried out with the rotated grating is that, when a cylindrical lens is rotated in the $E_2$ plane, only the vertical grating scans the principal curvature during the maximum rotation. The principal curvatures are not scanned with the rotated gratings during the maximum rotation.

LIST OF REFERENCE NUMBERS/LIST OF VARIABLES 5 stationary coordinate system
7 circular disk
9 ellipse
10 windshield
11 point (volume element) of the windshield 10
11.1, 11.2 point (volume element) of the windshield 10
11.3 point (volume element) of the windshield 10
12 light source
13, 14, 15 line grating
13', 14', 15' line grating
16 camera
17 optical axis of the camera 16
18, 19 edge beam
23 line grating of the imaging
25 coordinate system of the imaging
27 arrow
28, 29, 30 direction in which the line spacing of the particular line grating in the imaging is determined
31 y-axis (measured value in $m^{-1}$)
32 x-axis (angle of rotation in °)
33, 33' curve for the measured value $M_r$
33", 33'", curve for the measured value $M_r$
33"" curve for the measured value $M_r$
34, 34' curve for the measured value $M_h$
34", 34'" curve for the measured value $M_h$
34"" curve for the measured value $M_h$
35, 35' curve for the measured value $M_l$
35", 35'" curve for the measured value $M_l$
35"" curve for the measured value $M_l$
41 y-axis (amplification factor)
42 x-axis (angle of inclination in °)
47 curve for the amplification factor for glass (refractive index 1.5)
a, $a_o$, $a_u$ distance of windshield 10 from the line grating 14
d line spacing of the line grating 23 of the imaging
$d_s$ line spacing of the line grating 23 of the imaging measured in a direction perpendicular to the line grating 13
e, $e_1$, $e_1$" coordinates of a point on the line grating 13
$e_2$, $e_2$", s coordinates of a point on the line grating 13
F amplification factor
f focal length of a lens
g line spacing of the line grating 13
k curvature
k1, k2 curvature in the direction of the main axes
L2, L3 distance
$M_h$, $M_l$, $M_r$ measured values of the line grating imaging
n index of refraction/refractive index
S2, S3 distance
V1, Vr, Vl distance of a displacement
x, x', x", y, y', y", z, z" coordinates
β angle of rotation of the line grating 23 of the imaging for the stationary coordinate system
γ angle in the stationary coordinate system 5
ξ angle of inclination of the windshield 10 relative to the optical axis 17
ϵ, $\epsilon_1$, $\epsilon_2$ angle of rotation of the line grating 13 relative to the horizontal line grating 14
ϕ angle of rotation of the lens relative to the stationary coordinate system 5
λ, $\lambda_1$, $\lambda_2$ angle of rotation of the line grating 15 relative to the horizontal line grating 14
ν, μ factors of the imaging
σ angle of rotation of the line grating 13 relative to the stationary coordinate system 5

What is claimed is:

1. A method for determining a refractive power of a large-surface-area transparent object, the method comprising the steps of:

capturing a first imaging of a first line grating through the transparent object using a camera at at least one predetermined point of the transparent object;

using the central processing unit to determine a line spacing of the first imaging transverse to lines of the first line grating at the at least one predetermined point;

capturing a second imaging of a second line grating and a third imaging of a third line grating through the object using the camera, wherein lines of the second line grating extend at an angle not equal to 0° with respect to the lines of the first line grating and lines of the third line grating extend at an angle not equal to 0° with respect to the lines of the first line grating and extend at an angle not equal to 0° with respect to the lines of the second line grating;

using the central processing unit to determine respective line spacings of the second imaging and the third imaging transversely to the respective lines of the second line grating and third line grating, based on the second imaging and the third imaging and a rotation of the lines relative to the respective second line grating and third line grating; and using the central processing unit to calculate the refractive power in every azimuthal direction at the at least one predetermined point of the transparent object based on the determined line spacings and the rotation of the lines relative to the respective first line grating, second line grating and third line grating.

2. The method according to claim 1, wherein determining the line spacing for the first imaging is carried out perpendicular to the first line grating, determining the line spacing for the second imaging is carried out perpendicular to the second line grating and determining the line spacing for the third imaging is carried out perpendicular to the third line grating.

3. The method according to claim 1, further comprising moving the transparent object past the first line grating, the second line grating and the third line grating one after the other, and past the associated camera.and the first line grating, the second line grating and the third line grating extend parallel to one another.

4. The method according to claim 3, wherein the first line grating, the second line grating and the third line grating extend parallel to one another.

5. The method according to claim 1, wherein the first line grating, the second line grating and the third line grating are generated by a light wall having a matrix of light source elements.

6. The method according to claim 5, wherein the light source elements comprise light emitting diodes (LEDs) or organic light emitting diodes (OLEDs).

7. The method according to claim 1, wherein an inclination of the transparent object with respect to an optical axis of the camera is additionally taken into account in the calculation of the refractive power in every azimuthal direction at the at least one predetermined point.

8. The method according to claim 1, wherein the large-surface-area transparent object comprises any of a windshield, a visual aid, a cockpit and a helmet visor.

9. A device for determining a refractive power of a large-surface-area transparent object, comprising:
a camera;
a central processing unit;
a first line grating defined by first grating lines;
a second line grating defined by second grating lines, which second grating lines extend at an angle not equal to 0° with respect to the lines of the first line grating; and
a third line grating defined by third grating lines, which third grating lines extend at an angle not equal to 0° with respect to the lines of the first line grating and with respect to the lines of the second line grating;
wherein the camera captures a first imaging of the first line grating through the transparent object at at least one predetermined point of the object,
wherein the central processing unit processes the first imaging to determine a line spacing of the first imaging transversely to the first grating lines at the particular point;
wherein the camera captures a second imaging of the second line grating and a third imaging of the third line grating through the transparent object; and
based on the second imaging and the third imaging, the central processing unit determines a line spacing of the second imaging transversely to the second grating lines and a line spacing of the third imaging transversely to the third grating lines; and
based on the determined line spacings and with consideration for the rotation of the lines relative to the respective line grating, the central processing unit determines the refractive power in every azimuthal direction at the at least one predetermined point of the transparent object.

10. The device according to claim 9, wherein one or more of the first line grating, the second line grating and the third line grating extend parallel to one another or are disposed in a common plane.

11. The device according claims 9, wherein the camera is a matrix camera or a line scan camera.

12. The device according to claim 9, wherein the large-surface-area transparent object comprises any of a windshield, a visual aid, a cockpit and a helmet visor.

13. The device according to claim 9, wherein a separate camera is provided for each line grating of the first line grating, the second line grating and the third line grating.

14. The device according to claim 9, further comprising a light wall having a matrix made from light source elements comprising light emitting diodes (LEDs) or organic light emitting diodes (OLEDs) generates the first line grating, the second line grating and the third line grating one after the other by switching.

15. The device according to claim 14, wherein the light source elements comprise light emitting diodes (LEDs) or organic light emitting diodes (OLEDs).

* * * * *